(12) United States Patent
Sojka et al.

(10) Patent No.: US 6,491,953 B1
(45) Date of Patent: Dec. 10, 2002

(54) CONTROLLED RELEASE COMPOSITIONS AND METHOD

(75) Inventors: Milan F. Sojka, Algonquin, IL (US); Ralph Spindler, Lake Zurich, IL (US)

(73) Assignee: Amcol International Corporation, Arlington Heights, IL (US)

( * ) Notice: Subject to any disclaimer, the term of this patent is extended or adjusted under 35 U.S.C. 154(b) by 0 days.

(21) Appl. No.: 09/479,764

(22) Filed: Jan. 7, 2000

Related U.S. Application Data

(60) Provisional application No. 60/115,586, filed on Jan. 12, 1999.

(51) Int. Cl.[7] .............................. A61K 9/14; A61K 9/16; A61K 9/50; A61K 31/355; A61K 31/34
(52) U.S. Cl. ..................... 424/490; 424/400; 424/401; 424/489; 424/497; 424/498; 424/500; 424/501; 424/502; 514/458; 514/474; 514/725; 514/844; 514/963; 514/964; 514/965
(58) Field of Search .................................. 424/400, 401, 424/489, 490, 497, 498, 500, 501, 502; 514/458, 474, 725, 844, 963, 964, 965

(56) References Cited

U.S. PATENT DOCUMENTS

| | | | | |
|---|---|---|---|---|
| 5,208,038 A | * | 5/1993 | Gressani et al. ............ 424/489 |
| 5,316,774 A | * | 5/1994 | Eury et al. ................... 424/501 |
| 5,358,719 A | * | 10/1994 | Mellul et al. ................ 424/497 |
| 5,387,411 A | | 2/1995 | Abrutyn et al. ............... 424/47 |
| 5,559,202 A | | 9/1996 | Yoshikawa .................. 526/207 |
| 5,677,407 A | | 10/1997 | Sojka ....................... 526/323.2 |
| 5,692,302 A | * | 12/1997 | Martin et al. .................. 30/41 |
| 5,712,358 A | | 1/1998 | Sojka ....................... 526/323.2 |
| 5,753,261 A | * | 5/1998 | Fernandez et al. .......... 424/450 |
| 5,777,054 A | | 7/1998 | Sojka ....................... 526/323.2 |
| 5,830,960 A | * | 11/1998 | Sojka ....................... 526/194 |
| 5,830,967 A | | 11/1998 | Sojka ....................... 526/323.2 |
| 5,834,577 A | | 11/1998 | Sojka ....................... 526/323.2 |
| 5,837,790 A | * | 11/1998 | Sojka ....................... 526/323.2 |
| 5,888,930 A | * | 3/1999 | Smith et al. ................ 501/116 |
| 5,955,552 A | | 9/1999 | Sojka ........................... 526/88 |
| 6,024,943 A | * | 2/2000 | Ness et al. ..................... 424/59 |
| 6,107,429 A | * | 8/2000 | Sojka ....................... 526/323.2 |
| 6,248,849 B1 | * | 6/2001 | Sojka ....................... 526/336 |

FOREIGN PATENT DOCUMENTS

WO   WO 96/14058   5/1996

\* cited by examiner

Primary Examiner—Jose' G. Dees
Assistant Examiner—Marina Lamm
(74) Attorney, Agent, or Firm—Marshall, Gerstein & Borun

(57) ABSTRACT

A controlled release composition comprising an adsorbent polymer, an active agent, and a release retardant is disclosed. The composition has an improved ability to release the active agent over an extended time period.

12 Claims, 1 Drawing Sheet

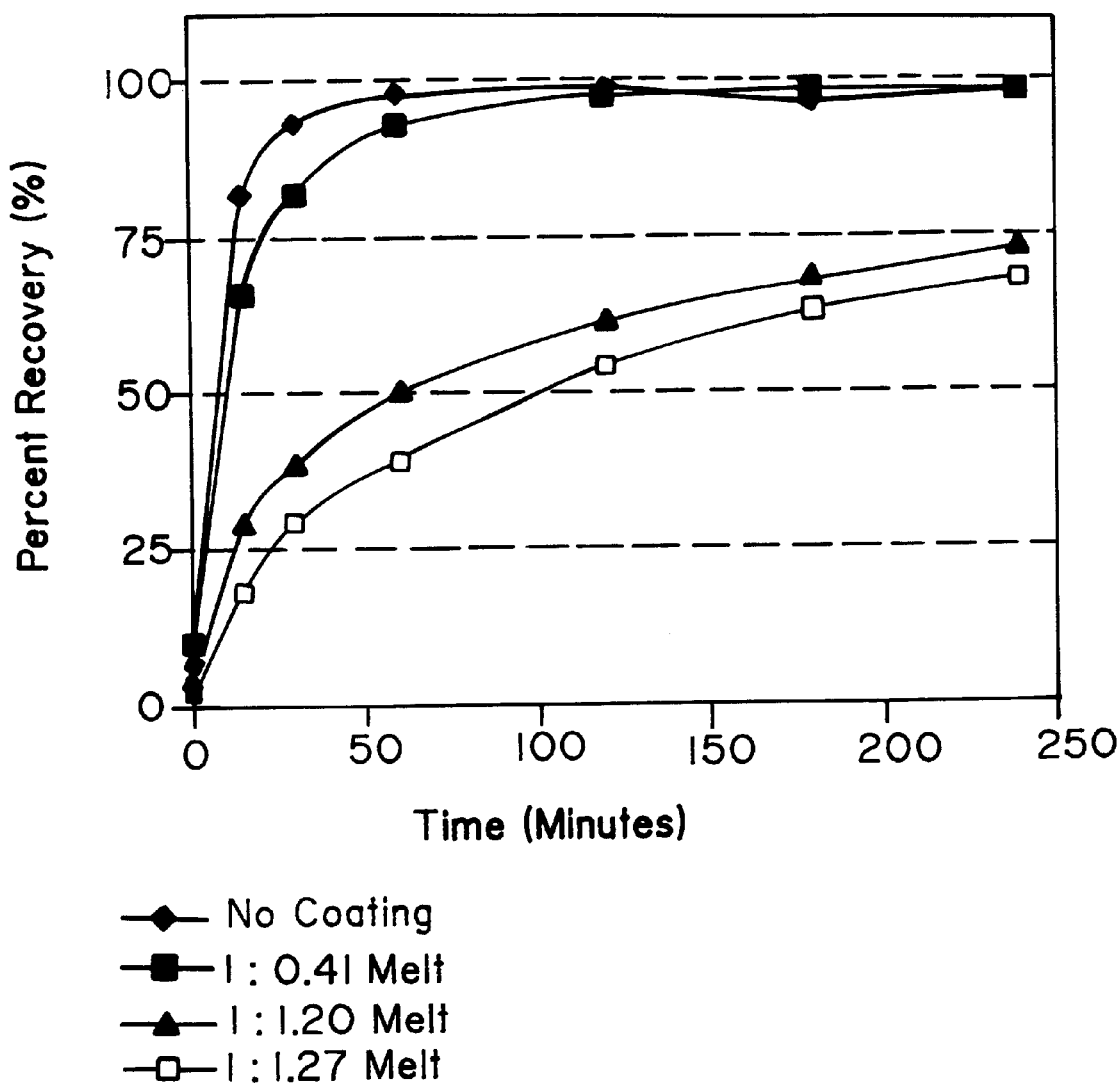

000
CONTROLLED RELEASE COMPOSITIONS AND METHOD

CROSS-REFERENCE TO RELATED APPLICATIONS

This application claims the benefit of provisional application Serial No. 60/115,586 filed Jan. 12, 1999.

FIELD OF THE INVENTION

The present invention relates to the controlled release of an active agent from a composition over an extended time. More particularly, the present invention relates to a composition that exhibits improved controlled release of an active agent, wherein the composition comprises an adsorbent bent polymer, an active agent, and a release retardant.

BACKGROUND OF THE INVENTION

The controlled release of an active agent, such as a drug or cosmetic compound, improves the safety, efficacy, and reliability of a treatment regimen that utilizes the active agent. Conventional dosage forms for delivering an active agent often provide a wide variation in the amount of active agent that is available during treatment. Consequently, the treatment regimen requires multiple doses such that the concentration of active agent is maintained at its minimum effective level. In particular, conventional dosage forms quickly release the active agent, which causes a sharp increase in active agent concentration to a peak, followed by a sharp decline in active agent concentration. This wide swing in active agent concentration provides acceptable results at peak or near peak concentrations, but inadequate treatment at lesser concentrations.

This problem can be overcome by administering a lower dose of an active agent in a conventional delivery system at more frequent intervals. However, individuals find such treatment regimens inconvenient, which leads to eliminating or delaying treatment doses, thereby adversely affecting the efficacy of the treatment.

In contrast, controlled release of an active agent regulates the release rate of the active agent and reduces the frequency of treatment doses, thereby improving compliance with the treatment regimen. Ideally, a controlled release of an active agent provides a predictable amount of the active agent for effective treatment, and controls the rate of active agent release over a predetermined time. The controlled release of an active agent can occur at a constant rate, or at a constant declining rate, at some other specified rate or pattern to achieve an efficacious release of the active agent.

The controlled release of an active agent has several advantages including fewer compliance problems during the treatment regimen, utilizing less of the active agent during treatment, improving efficacy of the treatment, and an overall cost savings. Although such benefits are recognized in the art, it has been difficult to provide compositions that achieve a controlled release of an active agent.

It has been especially difficult to achieve a controlled release of a water-soluble active agent when the water-soluble agent is a component of an aqueous controlled release composition, or when the water-soluble agent, in its controlled release form, is subjected to an aqueous medium. In these situations, the water-soluble agent has a tendency to be released too quickly from the composition.

Conversely, it is difficult to achieve a controlled release of an oil-soluble active agent when the oil-soluble active agent is a component of an oil-based controlled release composition or when the oil-soluble active agent, in its controlled release form, is subjected to a nonaqueous medium. In this situation, the oil-soluble agent has a tendency to be released too quickly from the composition.

In particular, a water-soluble or an oil-soluble active agent can be converted into its controlled release form by adsorbing the active agent onto an adsorbent polymer. The resulting controlled release form of the active compound can be formulated into a solid composition, e.g., a tablet or powder, a semisolid composition, e.g., a cream or gel, or a liquid composition, e.g., an emulsion or dispersion. Prior compositions have demonstrated a premature release of a water-soluble active agent when the controlled release form of the active agent is incorporated into an aqueous medium, like an emulsion, or when a semisolid or solid composition contacts an aqueous medium. Similarly, there is a premature release of an oil-soluble active agent when the controlled release form of the active agent is incorporated into a nonaqueous medium, like a body oil, or when the composition contacts a nonaqueous medium.

The present invention is directed to over-coming the problem of premature release of an active agent from controlled release compositions.

SUMMARY OF THE INVENTION

The present invention is directed to compositions that provide a controlled release of an active agent, including water-soluble and oil-soluble active agents. More particularly, the present invention is directed to a controlled release composition comprising an adsorbent polymer, an active agent, and a release retardant.

Therefore, one aspect of the present invention is to provide a controlled release composition comprising an adsorbent polymer, an active agent that is absorbed onto the adsorbent polymer, and a release retardant that imparts improved controlled release properties to the composition.

Another aspect of the present invention is to provide a controlled release composition comprising (a) an adsorbent polymer, having adsorbed there-to at least an equal weight amount, and typically several times the weight, of the adsorbent polymer of (b) a water-soluble or oil-soluble active agent, and (c) a release retardant that coats and/or is adsorbed onto the adsorbent polymer and active agent.

Yet another aspect of the present invention is to provide a controlled release composition comprising a water-soluble active agent, wherein the composition is in the form of an emulsion and exhibits a controlled release and delivery of the water-soluble agent.

Another aspect of the present invention is to provide a controlled release composition comprising an oil-soluble active agent, wherein the composition is based on a nonaqueous solvent, like an oil, and exhibits controlled release and delivery of the oil-soluble agent.

Another aspect of the present invention is to provide a controlled release composition containing an active ingredient selected from the group consisting of a skin care compound, a topical drug, an antioxidant, a dye, a self-tanning compound, an optical brightener, a deodorant, a fragrance, a sunscreen, a pesticide, a drug, and similar compounds, and mixtures thereof.

These and other aspects and novel features of the present invention will become apparent from the following detailed description of the preferred embodiments.

BRIEF DESCRIPTION OF THE FIGURES

FIG. 1 contains plots of percent recovery of active agent vs. time for adsorbent polymer-sali-cyclic acid combinations, either untreated or treated with stearyl alcohol.

DETAILED DESCRIPTION OF THE PREFERRED EMBODIMENTS

A controlled release composition of the present invention comprises: (a) an adsorbent polymer, (b) an active agent, and (c) a release retardant. The composition can be a solid composition in the form of a powder, or tablet, for example; a semisolid, like a cream or gel, for example; or a liquid, like an emulsion or dispersion, for example.

More particularly, the controlled release compositions comprise an adsorbent polymer having an active agent adsorbed thereto. The weight amount of active agent adsorbed onto the adsorbent polymer at least equals the weight of the adsorbent polymer, and typically is several times the weight of the adsorbent polymer. The active agent can be water soluble or oil soluble.

A release retardant then is applied to the adsorbent polymer-active agent combination to adsorb onto the polymer and/or coat the polymer and active agent. If the active agent is water soluble, the release retardant preferably is hydrophobic. If the active agent if oil soluble, the release retardant preferably is hydrophilic.

As used herein, the term "water-soluble compound" is defined as a compound having a solubility in water of at least 0.5 g per 100 grams of water at 25° C. Similarly, "oil-soluble compound" is defined as a compound having a solubility in mineral oil of at least 0.5 g per 100 grams of mineral oil at 25° C. The terms "water-dispersible" and "oil-dispersible" are defined as compounds having a solubility, at 25° C., in 100 g of water or mineral oil, respectively, of about 0.1 to about 0.5 g.

The adsorbent polymer-active agent-release retardant composition can be used as is, in a powder or tablet form, as a controlled release composition for a time extended delivery of the active agent. Similarly, the adsorbent polymer-active agent-release retardant composition can be formulated with other ingredients to provide a semisolid or a liquid controlled release composition for a time extended delivery of the active agent. For example, the controlled release composition can be applied topically, such that the active ingredient, e.g., an antioxidant, is slowly released from the adsorbent polymer, over an extended time, to perform its intended function.

Surprisingly, the present controlled release compositions are sufficiently stable, even in liquid form, such that the compositions retain their controlled release properties until administered, e.g., applied, to the skin. Previously, liquid controlled release compositions, like those containing a water-soluble active ingredient, exhibited poor controlled release properties because water present in the composition displaced the active agent from the adsorbent polymer, thereby solubilizing or dispersing the active agent. A similar disadvantage is observed with respect to liquid controlled release compositions containing an oil-soluble active ingredient and having an oil present. In either case, the active agent becomes available for immediate use, but is not available for a controlled release from the absorbent polymer after application of the controlled release composition.

The individual components of the present controlled release compositions are discussed in more detail below.

1. Adsorbent Polymers

An adsorbent polymer used in the present controlled release compositions has an ability to adsorb several times its weight of a solid or liquid compound, such as an active agent of the present invention. The polymer typically is in the form of a microparticle that is capable of entrapping a solid or liquid compound, either hydrophilic and/or hydrophobic.

One preferred class of adsorbent polymers is prepared by a suspension polymerization technique, as set forth in Sojka U.S. Pat. Nos. 5,677,407; 5,712,358; 5,777,054; 5,830,967; and 5,834,577, each incorporated herein by reference. Another preferred class of adsorbent polymers is prepared by a precipitation polymerization technique, as set forth in Sojka U.S. Pat. Nos. 5,830,960 and 5,837,790, both incorporated herein by reference.

In particular, the adsorbent polymer microparticles prepared by the suspension polymerization technique are a highly porous and highly crosslinked polymer in the form of open (i.e., broken) spheres and sphere sections characterized by a mean unit particle size of about 0.5 to about 3000 microns, preferably about 1 to about 300 microns, more preferably about 0.5 to about 100 microns, and most preferably about 0.5 to about 80 microns. A significant portion of the spheres is about 20 microns in diameter.

The microparticles are oil and water adsorbent, and have an extremely low bulk density of about 0.008 gm/cc to about 0.1 gm/cc, preferably about 0.009 gm/cc to about 0.07 gm/cc, and more preferably about 0.0095 gm/cc to about 0.04–0.05 gm/cc. The microparticles are capable of holding and releasing oleophilic (i.e., oil soluble), as well as hydrophilic (i.e., water soluble), active agents, individually, or both oleophilic and hydrophilic compounds simultaneously.

The adsorbent polymer microparticles made by the suspension polymerization technique include at least two polyunsaturated monomers, preferably allyl methacrylate and an ethylene glycol dimethacrylate, and, optionally, monounsaturated monomers. The microparticles are characterized by being open to their interior, due to either particle fracture upon removal of a porogen after polymerization or to subsequent milling. The microparticles have a mean unit diameter of less than about 50 microns, preferably less than about 25 microns, and have a total adsorption capacity for organic liquids, e.g., mineral oil, that is at least about 72% by weight, preferably at least about 93% by weight, and an adsorption capacity for hydrophilic compounds and aqueous solutions of about 70% to about 89% by weight, preferably about 75% to about 89% by weight, calculated as weight of material adsorbed divided by total weight of material adsorbed plus dry weight of polymer. In a preferred embodiment, the broken sphere microparticles are characterized by a mean unit diameter from about 1 to about 50 microns, more preferably from about 1 to about 25 microns, most preferably, from about 1 to about 20 microns.

A preferred adsorbent polymer prepared by the suspension polymerization technique is set forth below in Example 1.

EXAMPLE 1

(Polypore™ E 200)

METHOCEL A4C Premium (5.25 grams) was dissolved in 573.3 grams of water in a 2000 ml three-necked vessel equipped with a stirrer, thermometer, condenser, and argon purge. A solution of 40.92 grams of allyl methacrylate, 76.48 grams of ethylene glycol dimethacrylate, 765.20 grams of n-heptane, and 2.33 grams of VAZO 52 was purged with argon for 10 minutes. The resulting mixture was slowly added to the stirred (1,500 rpm) aqueous solution of the METHOCEL at 23° C. under argon. The temperature was raised to 46° C. with constant agitation when precipitation started. Massive polymerization was observed at 53° C. The reaction mixture then was heated to 60° C. to 65° C., and was held at that temperature for an additional six hours. Thereafter, the reaction mixture was subjected to steam distillation to remove the heptane and residual monomers. The resulting copolymer was separated from the reaction mixture by filtration. The separated copolymer was washed with deionized water and dried in an oven at 80° C. The dried copolymer was an odorless, white, soft powder having a total adsorption capacity for light mineral oil of 11.1 grams/1 gram, an apparent density of 0.032 g/cc, a mole ratio of allyl methacrylate:ethylene glycol dimethacrylate 1:1.22, and a corresponding ratio mole percent 46:54.

An adsorbent polymer prepared by the precipitation polymerization technique is a highly porous and highly cross-linked oleophilic polymer in the form of individual microparticles, aggregates of microparticles, and clusters of aggregates (agglomerates) of microparticle spheres. The microparticles have an oil sorbency of at least about 80% by weight or greater, based on the weight of adsorbed oil plus adsorbent polymer. The assemblies of oil adsorbent microparticle aggregates produced by the process have sizes up to about 3000 microns, preferably less than about 1000 microns. The microparticles have extremely low apparent bulk densities in the range of about 0.02 gm/cc to about 0.1 gm/cc, preferably about 0.03 gm/cc to about 0.07 gm/cc, and more preferably about 0.03 gm/cc to about 0.04–0.05 gm/cc.

The microporous, oil-adsorbent microparticles and microparticle aggregates of adsorbent polymer comprise at least one and preferably at least two polyunsaturated monomers, preferably allyl methacrylate and an ethylene glycol dimethacrylate, and optionally a monounsaturated monomer. The microparticles and microparticle aggregates are characterized by having a void volume surrounded by aggregated microparticle spheres and having a mean unit microparticle diameter of less than about 10 microns, preferably less than about 8 microns, having a total adsorption capacity for organic liquids, e.g., mineral oil that is at least 80% by weight based on the total weight of adsorptive microparticles plus adsorbed oil. Preferably, the microparticles of adsorbent polymer have a total sorption capacity for mineral oil of about 82–93% by weight, more preferably about 84% by weight or greater, most preferably about 85–93% by weight or greater. In a preferred embodiment, the microparticle assemblies, or aggregated spheres of microparticles, are characterized by a mean unit diameter from about 5 to about 500 microns ($\mu$m), preferably about 5 to about 100 $\mu$m, some aggregates having a diameter of about 2 to about 100 $\mu$m, others having diameters from about 20 to about 80 microns.

The adsorbent polymer comprises microporous and oil-adsorbent microparticles and aggregates thereof in the form of microparticle spheres, and aggregates thereof, in the form of spheres having a mean unit diameter of less than about 2 microns, preferably less than about 1 micron. The phrase mean "unit diameter" refers to mean diameter of the individual particle and not to the diameter of agglomerates. The mean unit diameter of the individual microparticles is more preferably from about 0.5 to about 2 microns, most preferably, from about 0.5 to about 1 micron, while the mean diameter of the aggregates preferably is about 5 to about 20 microns, preferably about 5 to about 12 microns.

The microparticles of adsorbent polymer are a white powder and constitute free-flowing discrete solid particles, even when loaded with a lipophilic material to their "free flowing" sorption capacity.

A preferred adsorbent polymer prepared by the precipitation polymerization method is described in Example 2 herein, having mole ratio of about 1:1.2 allyl methacrylate-:monoethylene glycol dimethacrylate.

EXAMPLE 2

(Polypore™ L 200)

An oleophilic porous copolymer was produced using a precipitation polymerization technique, i.e., by slowly mixing, in a 2-liter polymerization reactor equipped with a paddle-type stirrer, 12.55 grams of allyl methacrylate (46 mole percent), and 23.45 grams of ethylene glycol dimethacrylate (54 mole percent). Cyclomethicone DC 244 Fluid (Dow Corning, Midland, Mich.) was added to the reactor in the amount of 564 grams as the solvent. The monomers were soluble in the solvent. The mixture, including monomers, solvent, and 0.72 grams of catalytic initiator VAZO 52, was purged with argon. At the stirring speed of 30 rpm, the system was heated at about 45° C. until polymerization was initiated, at which time the temperature was increased to 65° C., and maintained for six hours in order to complete the polymerization. During this time, the polymer precipitated from the solution. The polymerization produced unit particles of a diameter less than about one micron. Some of the unit particles adhered further and were fused and welded one to another forming aggregates of loosely held assemblies of agglomerates of the order of the magnitude of about 5 to about 100, preferably about 5 to about 80 microns, microns in diameter. The mixture was filtered to remove excess solvent, and a wet powder cake was dried in a vacuum oven. A dry hydrophobic polymeric powder consisting of unit particles, agglomerates, and aggregates was isolated, having a total adsorption capacity for light mineral oil of 11.2 grams per gram of polymer, and apparent density of 0.034 g/cm$^3$.

Other adsorbent polymers also can be used in the controlled release compositions of the present invention. The only limitation on the adsorbent polymer is an ability at adsorb at least an equal weight amount of a solid or a liquid active agent, and preferably an ability to adsorb a greater than equal weight amount of an active agent. The adsorbent polymer typically adsorbs about 4 to about 5 times its weight of an active agent, and often about 10 times, and up to about 20 times, its weight of an active agent.

In addition, the adsorbent polymer is not limited to copolymers disclosed above. Several other useful adsorbent polymers are available commercially, for example, MICRO-SPONGE POLYTRAP, available from Advanced Polymer Systems, Redwood City, Calif., and Poly-HIPE polymers available from Biopore Corp., Mountain View, Calif.

The amount of adsorbent polymer present in a controlled release composition is related to the amount of active agent in the composition. The amount of active agent required to perform its intended function first is determined, then the amount of adsorbent polymer is determined based on considerations such as the identity of the adsorbent polymer and active agent, and the ability of the adsorbent polymer to adsorb the active agent. Such a determination is easily performed by persons skilled in the art. As stated above, the maximum weight amount of adsorbent polymer present in the composition is equal to the weight amount of active agent in the composition. The minimum weight amount of adsorbent polymer in the composition is about 20 times less than the weight amount of active agent in the composition.

2. Active Agent

In accordance with an important feature of the present invention, the active agent can be any of a wide variety of compounds, either water soluble or oil soluble. Often, the active agent is a topically active compound. The controlled release composition, therefore, can be applied to the skin, and the active agent then performs its intended function as it is released from the controlled release composition over time and contacts the skin.

Although the following discussion is directed primarily to topically active compounds, the active agent can be a different type of compound, such as a fragrance, which is control released to act as a room deodorizer, or a pesticide, which is released in a controlled manner for extended insecticidal or herbicidal activity, or similar types of active agents, like drugs and therapeutic agents, that are used in controlled release applications.

The active agent often is a water-soluble or water-dispersible compound, i.e., is hydrophilic. However, the active agent can be oil soluble or oil dispersible, i.e., is hydrophobic. In other embodiments, the active agent is a mixture of compounds, either all hydrophilic, all oleophilic, or a mixture of hydrophilic and oleophilic compounds. As discussed hereafter, the release retardant also may contribute to the efficacy of the composition.

The active agent is present in the controlled release composition in an amount to perform its intended function, typically in an amount of about 0.1% to about 30%, by weight, of the composition when in liquid form, and about 50% to about 95%, by weight, of the composition when in solid form. Semisolid forms of a controlled release composition contain about 0.1% to about 75%, by weight, of the active agent. Persons skilled in the art are aware of the amount of active agent needed to perform its intended function, and are capable of determining the amount active agent to incorporate into the composition based on the form, e.g., solid, semisolid, or liquid, of the composition.

With respect to topically active agents, such agents are intended to be applied to the skin, or hair, and allowed to remain on the skin for an extended time period to allow a controlled release of the active agent to perform its function.

The topically active agent, therefore, can be one of, or a mixture of, a cosmetic compound, a medicinally active compound, or any other compound that is useful upon topical application to the skin or hair. Such topically active agents include, but are not limited to, hair-growth promoters, deodorants, skin-care compounds, antioxidants, hair dyes, antibacterial compounds, antifungal compounds, anti-inflammatory compounds, topical anesthetics, sunscreens, and other cosmetic and medicinal topically effective compounds.

For example, a skin conditioner can be the active agent of a composition of the present invention. Skin conditioning agents include, but are not limited to, humectants, such a fructose, glucose, glycerin, propylene glycol, glycereth-26, mannitol, and urea, pyrrolidone carboxylic acid, hydrolyzed lecithin, coco-betaine, cysteine hydrochloride, glucamine, PPG-15, sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E, and D, amino-functional silicones, ethoxylated glycerin, alpha-hydroxy acids and salts thereof, fatty oil derivatives, such as PEG-24 hydrogenated lanolin, almond oil, grape seed oil, and castor oil, and mixtures thereof. Numerous other skin conditioners are listed in the *CTFA Cosmetic Ingredient Handbook*, First Ed., J. Nikotakis, ed., The Cosmetic, Toiletry and Fragrance Association (1988), (hereafter *CTFA Handbook*), pages 79–84, incorporated herein by reference.

In addition, the topically active agent can be a hair dye, such as, but not limited to, m-aminophenol hydrochloride, p-aminophenol sulfate, 2,3-diaminophenol hydrochloride, 1,5-naphthalene-diol, p-phenylenediamine hydrochloride, sodium picramate, cationic dyes, anionic dyes, FD&C dyes, like Blue No. 1, Blue No. 2, Red No. 3, Red No. 4, or Red No. 40, D&C dyes, like Yellow No. 10, Red No. 22, or Red No. 28, and pyrogallol. Numerous other hair dyes are listed in the *CTFA Handbook*, pages 70–71, incorporated herein by reference.

The topically active agent also can be an antioxidant, like ascorbic acid or erythorbic acid, or a fluorescent whitening agent or optical brightener, like a distyrylbiphenyl derivative, stilbene or a stilbene derivative, a pyralozine derivative, or a coumarin derivative. In addition, a self-tanning compound, like dihydroxy acetone, or a hair growth promoter can be the topically active agent.

The topically active agent also can be a deodorant or antiperspirant compound, such as an astringent salt or a bioactive compound. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate, or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine, or iodine; x is about 2 to about 5; x+y is about 6, wherein x and y are not necessarily integers; and X is about 1 to about 6. Exemplary zirconium compounds include zirconium oxy salts and zirconium hydroxy salts also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2-nz is greater than or equal to 0; and L is selected from the group consisting of halides, nitrate, sulfamate, sulfate, and mixtures thereof.

Exemplary deodorant compounds, therefore, include, but are not limited to, aluminum bromohydrate, potassium alum, sodium aluminum chloro-hydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, chlorophyllin copper complex, numerous other useful antiperspirant compounds listed in the *CTFA Handbook* at page 56, incorporated herein by reference, and mixtures thereof. The active agent also can be a fragrance that acts as a deodorizer by masking malodors. Numerous fragrance compounds are listed in the *CTFA Handbook*, pages 69–70, incorporated herein by reference.

In addition, other compounds can be included as the topically active agent in an amount sufficient to perform their intended function. For example, if the composition is intended to be a sunscreen, then compounds such as benzophenone-3, trihydroxycinnamic acid and salts, tannic acid, uric acids, quinine salts, dihydroxy naphtholic acid, an anthranilate, diethanolamine methoxycinnamate, p-aminobenzoic acid, phenylbenzimidazole sulfonic acid, PEG-25, p-aminobenzoic acid, or triethanolamine salicylate can be used as the active agent.

Further, sunscreen compounds such as dioxybenzone, ethyl 4-[bis(hydroxypropyl)]amino-benzoate, glyceryl aminobenzoate, homosalate, methyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-6, benzophenone-12, isopropyl dibenzoyl methane, butyl methoxydibenzoylmethane, zotocrylene, or zinc oxide can be used as the active agent. Other sunscreen compounds are listed in *CTFA Handbook*, pages 86 and 87, incorporated herein by reference.

Similarly, topically active drugs, like antifungal compounds, antibacterial compounds, anti-inflammatory compounds, topical anesthetics, skin rash, skin disease, and dermatitis medications, and anti-itch and irritation-reducing compounds can be used as the active agent in the compositions of the present invention. For example, analgesics such as benzocaine, dyclonine hydrochloride, aloe vera, and the like; anesthetics such as butamben picrate, lidocaine hydrochloride, xylocaine, and the like; antibacterials and antiseptics, such as povidone-iodine, polymyxin b sulfate-bacitracin, zinc-neomycin sulfate-hydrocortisone, chloramphenicol, ethylbenzethonium chloride, erythromycin, and the like; antiparasitics, such as lindane; essentially all dermatologicals, like acne preparations, such as benzoyl peroxide, erythromycin benzoyl peroxide, clindamycin phosphate, 5,7-dichloro-8-hydroxyquinoline, and the like; anti-inflammatory agents, such as alclometasone dipropionate, betamethasone valerate, and the like; burn relief ointments, such as o-amino-p-toluenesulfonamide monoacetate, and the like; depigmenting agents, such as monobenzone; dermatitis relief agents, such as the active steroid amcinonide, diflorasone diacetate, hydrocortisone, and the like; diaper rash relief agents, such as methylbenzethonium chloride, and the like; emollients and moisturizers, such as mineral oil, PEG-4 dilaurate, lanolin oil, petrolatum, mineral wax, and the like; fungicides, such as butocouazole nitrate, haloprogin, clotrimazole, and the like; herpes treatment drugs, such as O-[(2-hydroxymethyl) methyl]guanine; pruritic medications, such as alclometasone dipropionate, betamethasone valerate, isopropyl myristate MSD, and the like; psoriasis, seborrhea, and scabicide agents, such as anthralin, methoxsalen, coal tar, and the like; steroids, such as 2-(acetyloxy)-9-fluoro-1', 2', 3', 4'-tetrahydro-11-hydroxypregna-1,4-dieno-[16,17-b] naphthalene-3,20-dione and 21-chloro-9-fluoro-1', 2', 3', 4'-tetrahydro-11b-hydroxypregna-1,4-dieno-[16,17-b] naphthalene-3,20-dione. Any other medication capable of topical administration, like skin bleaching agents, skin protestant, such as allantoin, and antiacne agents, such as salicylic acid, also can be incorporated in a composition of the present invention in an amount sufficient to perform its intended function. Other topically active compounds are listed in *Remington's Pharmaceutical Sciences*, 17th Ed., Merck Publishing Co., Easton, Pa. (1985), pages 773–791 and pages 1054–1058 (hereinafter *Remington's*), incorporated herein by reference.

In the preparation of a controlled release composition of the present invention, the active agent first is adsorbed onto the adsorbent polymer. The following examples illustrate adsorbing the active agent to the adsorbent polymer.

EXAMPLE 3

The copolymer powder of Example 1 was mixed with zinc pyrithione (solids having a particle size of 3 to 5 microns slurried in water) in an amount of 12 grams of slurry per one gram of the copolymer, then dried in an oven at 80° C. to evaporate water. The resulting dry product was a white, fine powder with 85% entrapped zinc pyrithione, i.e., 5.76 grams per gram. Zinc pyrithione was supplied by Ruetger Nease Company, as mixture of 48% of zinc pyrithione, 51% water, and 1% zinc chloride, and is used as antidandruff component in hair care products, e.g., antidandruff shampoos.

EXAMPLE 4

The copolymer of Example 1 was loaded with a methanol/salicylic acid solution in an amount of 12 grams per gram, and dried in an oven at 80° C. to evaporate the methanol. The resulting dry product was a white, fine powder, with 74% entrapped salicylic acid, i.e., 2.8 grams per gram. Entrapped salicylic acid is not light sensitive, nor explosive. Salicylic acid is an antiseptic and antifungal agent.

EXAMPLE 5

Retinol was dissolved in same amount of ether. The solution (5.5 grams) was adsorbed on 1 gram of the adsorbent polymer of Example 1. Thereafter, ether was evaporated under vacuum and a free-flowing light yellow powder was obtained. The adsorbed amount of retinol was 2.5 grams per gram, i.e., 71%. Usually retinol is in the form of sticky crystals, is light sensitive, and is skin irritant. Retinol is used in cosmetic formulations and as a vitamin.

The microparticles of Example 1 (POLYPORE™ E 200) also had various other solid and liquid hydrophilic and oleophilic materials adsorbed thereto, as shown in Table 1:

TABLE 1

| | Total (g/g) | Free-Flowing (g/g) |
|---|---|---|
| Mineral Oil | 10.4 | 8.1 |
| Artificial Sebum | 10.8 | 8.1 |
| Glycerin | 8.0 | 6.0 |
| Cyclomethicone (DC 244) | 12.0 | 9.6 |
| Isopropyl Myristate | 10.7 | 8.0 |
| Vitamin E Acetate | 7.2 | 5.6 |
| Benzophenone-3 | 12.3 | 9.2 |
| PEG 200 | 11.2 | 8.8 |
| Benzyl Acetate | 12.3 | 10.2 |
| Fragrance/Floral Lavender | 11.1 | 8.1 |
| Dimethicone (10 cps) | 10.6 | 8.5 |
| Dimethicone (200 cps) | 10.2 | 7.1 |
| Dirnethicone (350 cps) | 10.0 | 6.9 |
| Dirnethicone (1000 cps) | 10.0 | 6.9 |
| IRGASAN DP 300 (5-chloro-2-(2,4-dichlorophenoxy)phenol) | 10.0 | |

EXAMPLE 6

The copolymer of Example 2 was loaded with a methanol/salicylic acid solution to an amount of 12 grams per gram, and dried in an oven at 80° C. to evaporate methanol. The resulting dry product was a white, fine powder, with 78.3% entrapped salicylic acid, i.e., 2.8 grams per gram. The entrapped salicylic acid was not light sensitive, nor explosive, whereas free salicylic acid is both light sensitive and explosive.

EXAMPLE 7

Retinol was dissolved in an equal weight amount of ether, then 5.5 grams of the solution was adsorbed on 1 gram of the adsorbent polymer of Example 2. Thereafter, ether was evacuated under vacuum, and a free-flowing light yellow powder was obtained. The adsorbed amount of retinol was 2.75 grams per gram, i.e., 73%. Usually, retinol is in form of sticky crystals, is light sensitive, and a skin irritant.

The microparticles of Example 2 (POLYPORE™ L 200) also had various other solid and liquid active agents adsorbed thereto, as shown in Table 2:

TABLE 2

|  | Total (g/g) | Free-Flowing (g/g) |
| --- | --- | --- |
| Mineral Oil | 11.6 | 9.0 |
| Artificial Sebum | 12.6 | 9.5 |
| Glycerin | 10.0 | 7.6 |
| Cyclomethicone (DC 244) | 15.0 | 10.8 |
| Isopropyl Myristate | 11.4 | 9.5 |
| Vitamin E Acetate | 9.2 | 7.0 |
| Benzophenone-3 | 12.8 | 9.1 |
| PEG 200 | 13.2 | 9.8 |
| Benzyl Acetate | 12.7 | 9.9 |
| Fragrance (Floral Lavender) | 12.7 | 9.6 |
| Dimethicone (10 cps) | 14.1 | 10.5 |
| Dimethicone (200 cps) | 14.0 | 9.1 |
| Dimethicone (350 cps) | 12.5 | 8.9 |
| Dimethicone (1000 cps) | 12.1 | 8.6 |
| IRGASAN DP 300 (5-chloro-2-(2,4 dichlorophenoxy)phenol) | 10.7 | |

3. Release Retardant

The control release capabilities of the adsorbent polymer-active agent combination is adversely affected when the active agent is hydrophilic (i.e., is water soluble or dispersible) and the combination is incorporated into an aqueous liquid composition, or otherwise comes in contact with water. The water displaces at least a portion of the active agent, and especially water-soluble or water-dispersible active agents, from the adsorbent polymer. The displaced active agent then is in free form in solution, and, accordingly, performs its intended function as soon as the composition is applied. The displaced active agent, therefore, is unavailable for controlled release.

Similarly, when the adsorbent polymer-active agent combination contains an oleophilic (i.e., oil soluble or oil dispersible) active agent, the active agent is displaced when the combination is incorporated into an oil-based composition, or otherwise comes in contact with an oil or nonaqueous solvent. As discussed above with respect to a water-soluble active agent, the oil-soluble active ingredient then is in the free form, performs its intended function immediately, and is not available for controlled release.

To retard or eliminate displacement of the active agent from the adsorbent polymer, a release retardant is added to the adsorbent polymer-active agent combination. The release retardant typically is added after the adsorbent polymer-active agent combination is prepared. Alternatively, the release retardant can be added to adsorbent polymer simultaneously with the active agent.

Preferably, the release retardant is hydrophobic when the active agent is water soluble. Conversely, the release retardant preferably is hydrophilic when the active agent is oil soluble. The preferred combinations of active agent and release retardant are not essential to the present invention, because utilizing a hydrophilic release retardant with a water-soluble active agent, or a hydrophobic release retardant with an oil-soluble active agent, improves the controlled release properties of the composition.

The release retardant is adsorbed onto the adsorbent polymer and also coats the adsorbent polymer and the active agent. The release retardant, therefore, retards or eliminates a rapid displacement of the active agent from the adsorbent polymer by water or a nonaqueous solvent, thereby leaving the active agent in a "combined" form that is available for controlled release.

The amount of release retardant present in the controlled release composition is about 0.5% to about 30%, and preferably about 2% to about 20%, by weight of the composition. To achieve the full advantage of the present invention, the release retardant is present in an amount of about 5% to about 15%, by weight of the composition. Above about 30% by weight of the composition, no additional benefit is observed and the amount of release retardant can be sufficiently high to adversely affect controlled release of the active agent. Below about 0.5% by weight, the release retardant is not present in a sufficient amount to retard or eliminate a rapid displacement of the active agent from the adsorbent polymer.

The identity of the release retardant is not particularly limited. However, it is preferred that the release retardant is water insoluble, i.e., has a water-solubility of 0.1 g (gram) or less in 100 ml (milliliter) of water at 25° C., when the active agent is water soluble. It is also preferred that the release retardant is oil insoluble, i.e., has an oil-solubility of 0.1 g or less in 100 ml of mineral oil at 25° C., when the active agent is oil soluble. However, release retardants having oil or water solubility up to 20 g in 100 ml of mineral oil or water, respectively, can be used with water-soluble and oil-soluble active agents, respectively.

The release retardant is selected such that it does not adversely affect the active agent, e.g., is nonreactive and noninteractive with the active agent. The release retardant can be a solid at room temperature, i.e., 25° C., or can be a liquid. A liquid release retardant has a low volatility, i.e., has a boiling point of above 150° C. at one atmosphere. In many embodiments, the release retardant has cosmetic or medicinal properties which perform in conjunction with the active agent.

Accordingly, one class of useful release retardant is the fatty alcohols, i.e., alcohols having eight through twenty carbon atoms ($C_8$–$C_{20}$). Fatty alcohols ethoxylated with one to three moles of ethylene oxide also are useful hydrophobic compounds. Examples of fatty alcohols and ethoxylated fatty alcohols include, but are not limited to, behenyl alcohol, caprylic alcohol, cetyl alcohol, cetaryl alcohol, decyl alcohol, lauryl alcohol, isocetyl alcohol, myristyl alcohol, oleyl alcohol, stearyl alcohol, tallow alcohol, steareth-2, ceteth-1, cetearth-3, and laureth-2. Sterols, like lanolin alcohol, also can be used as the release retardant. Additional fatty alcohols and sterols are listed in the *CTFA Handbook*, pages 28 and 45, incorporated herein by reference.

Another useful class of release retardants are the $C_8$–$C_{20}$ fatty acids, including, but not limited to, stearic acid, capric acid, behenic acid, caprylic acid, lauric acid, myristic acid, tallow acid, oleic acid, palmitic acid, isostearic acid, and additional fatty acids listed in the *CTFA Handbook*, pages 27 and 28, incorporated herein by reference.

The release retardant also can be a hydro-carbon, like mineral oil, 1-decene dimer, a poly-decene, paraffin, petrolatum, or an isoparaffin, for example. Another class of release retardants is the waxes, like mink wax, montan wax, carnauba wax, and candelilla wax, for example, and synthetic waxes, like silicone waxes, polyethylene, and polypropylene. Additional hydrocarbons and waxes are listed in the *CTFA Handbook*, pages 31 and 49, incorporated herein by reference.

Fats and oils also are useful release retardants. Examples of fats and oils include, but are not limited to, lanolin oil, linseed oil, coconut oil, olive oil, menhaden oil, castor oil, soybean oil, tall oil, rapeseed oil, palm oil, and neatsfoot oil. Glyceryl esters of fatty acids also can be used as the release retardant, as can lanolin derivatives, such as hydrogenated lanolin, oleyl lanolate, lanolinamide DEA, and similar lanolin derivatives. Similarly, essential oils, like eucalyptus oil, peppermint oil, rose oil, clove oil, lemon oil, pine oil, and orange oil, can be used as the release retardant. Such essential oils also can serve as a fragrance. Additional fats, oils, and essential oils are listed in the *CTFA Handbook*, pages 23, 26, and 27, incorporated herein by reference.

An especially useful class of release retardants is the silicone oils, like dimethicone, and the functional silicone oils, like dimethicone copolyol. The silicone oils have a viscosity of about 10 centipoise (cps) to about 600,000 cps, and typically about 350 cps to about 10,000 cps, at 25° C. Examples of silicone oils include dimethicone, dimethicone copolyol, dimethiconol, simethicone, phenyl trimethicone, stearoxy dimethicone, tri-methylsilylamodimethicone, an alkyl dimethicone copolyol, and a dimethicone having polyoxyethylene and/or polyoxypropylene side chains.

Other classes of useful release retardants include poly(acids), like poly(lactic acid); polymeric ethers, both homo and block copolymers, like poly(ethylene oxide-b-propylene oxide); polyols, like sorbitol, ascorbic acid, and mannitol; salts of $C_8$–$C_{20}$ fatty acids, e.g., sodium, potassium, aluminum, calcium, and magnesium salts of fatty acids; alkanolamides; and synthetic polymers, like a urea/formaldehyde resin, a polyethyleneimine, a polyacrylamide, a polyacrylic acid and salts thereof, polyvinylpyrrolidone and copolymers thereof, a polyisoprene, or a polystyrene, for example. Additional polymeric ethers, alkanolamides, and synthetic polymers are listed in the *CTFA Handbook*, pp. 3, 4, 38, 39, 47, and 48, incorporated herein by reference.

The release retardant also can be a water-insoluble ester having at least 10 carbon atoms, and preferably 10 to about 32 carbon atoms. Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Suitable esters, therefore, include, for example, but are not limited to:

(a) aliphatic monohydric alcohol esters, including, but not limited to:
myristyl propionate,
isopropyl isostearate,
isopropyl myristate,
isopropyl palmitate,
cetyl acetate,
cetyl propionate,
cetyl stearate,
isodecyl neopentanoate,
cetyl octanoate,
isocetyl stearate;

(b) aliphatic di- and tri-esters of polycarboxylic acid, including, but not limited to:
diisopropyl adipate,
diisostearyl fumarate,
dioctyl adipate, and
triisostearyl citrate;

(c) aliphatic polyhydric alcohol esters, including, but not limited to:
propylene glycol dipelargonate;

(d) aliphatic esters of aromatic acids, including, but not limited to:
$C_{12}$–$C_{15}$ alcohol esters of benzoic acid,
octyl salicylate,
sucrose benzoate, and
dioctyl phthalate.

Numerous other esters are listed in the *CTFA Handbook*, at pages 24 through 26, incorporated herein by reference.

The release retardant also can be a biological polymer, a gum, a salt or derivative of a gum, or a carbohydrate. Examples of such release retardants include, but are not limited to, hyaluronic acid, potato starch, corn starch, rice starch, sodium hyaluronate, locust bean gum, tragacanth gum, xanthan gum, methylcellulose, hydroxyethylcellulose, karaya gum, carboxymethylcellulose, sucrose, sucrose laurate, dextrin, corn syrup, pectin, methyl gluceth-10, gelatin, algin, carrageenan, and mixtures thereof. Additional biological polymers, carbohydrates, gum, and salts and derivatives of gums are listed in the *CTFA Handbook*, at pp. 16, 19, 29, and 30, incorporated herein by reference.

Another class of release retardants is the sorbitan derivatives, like PEG-10 sorbitan laurate, PEG-20 sorbitan isostearate, PEG-3 sorbitan oleate, polysorbate 40, sorbitan stearate, and sorbitan palmitate, for example. Other sorbitan derivatives are listed in the *CTFA Handbook*, at page 44, incorporated herein by reference.

4. Optional Ingredients

The controlled release compositions of the present invention also can include optional ingredients traditionally included in cosmetic, medicinal, and other such compositions. These optional ingredients include, but are not limited to, dyes, fragrances, preservatives, antioxidants, detackifying agents, and similar types of compounds. The optional ingredients are included in the composition in an amount sufficient to perform their intended function.

The following examples and tests show the improved control release properties demonstrated by adding a release retardant to an adsorbent polymer-active agent combination.

EXAMPLE 8

First, an adsorbent polymer-active agent combination containing 40% by weight POLYPORE™ E 200 (Example 1) and 60% by weight l-ascorbic acid was prepared in a manner similar to the method set forth in Example 4.

A solution of paraffin oil (5 g) in 150 ml of methylene chloride ($CHCl_3$) was entrapped in a first 50 g portion of the polymer-ascorbic acid combination. The chloroform was evaporated to provide a controlled release composition containing 5 g of paraffin oil and 50 g of the polymer-ascorbic acid combination.

Similarly, to a second and third 50 g portion of the polymer-ascorbic acid combination was entrapped 5 g of a dimethicone (1,000 cps) (DC 200 Fluid available from Dow Corning Corp., Midland, Mich.) and 5 g of a silicone wax (AMS-C30, available from Dow Corning), respectively. The DC200 is a liquid and was entrapped neat, i.e., without solvent. The AMS-C30 is a solid that was melted at 85° C., then entrapped neat.

The stability of the three compositions was tested by adding individual portions of the three compositions to water at 25° C. and at 45° C. A control solution of 1-ascorbic acid in water discolored after four hours at 45° C. and after five days at room temperature. No discoloration was observed in any of the three controlled release compositions of the present invention over the same time period at either temperature. A polymer-ascorbic acid solution, without the addition of a release retardant, also discolored during the test. Accordingly, a release retardant protects and stabilizes an active agent adsorbed onto an adsorbent polymer.

Additional tests were performed to illustrate the beneficial effects a release retardant has on the controlled release of an active agent. In particular, POLYPORE™ E 200 (Example 1) was loaded with glycolic acid by admixing one gram of POLYPORE™ E 200 and a solution of 1 gram glycolic in 50 ml of methanol, stirring for 2.5 hours, then evaporating the methanol on a rotary evaporator. The resulting polymer-glycolic acid combination was dried at room temperature under vacuum.

To individual portions of the polymer-glycolic acid combination was added mineral oil or butanol at 1:1 and 2:1 weight ratios of mineral oil or butanol to the combination. The resulting compositions were added to water, and pH measurements were made to determine whether the mineral oil and/or butanol slowed the release of glycolic acid from the polymer-glycolic acid combination compared to the untreated polymer-glycolic acid combination.

The pH measurements showed that mineral oil provided a barrier between the polymer-glycolic acid combination and the water, and retarded displacement of glycolic acid from the adsorbent polymer, thereby providing an improved controlled release of the glycolic acid. These improved results were not observed with the butanol-treated sample, thereby showing that a release retardant achieves improved controlled release properties.

A similar series of tests was performed using salicylic acid adsorbed onto POLYPORE™ E 200 (Example 1). In particular, the following samples were prepared:

Sample 1-a 1:1.2 weight ratio of POLYPORE™ E loaded with 67% salicylic acid to stearyl alcohol (octadecanol) was prepared by melting the stearyl alcohol at 65° C. for one hour, then adding the melted alcohol to the polymer-salicylic acid combination, which had been heated to 65° C.

Sample 2-a 1:1 ratio of POLYPORE™ E loaded with 67% salicylic acid to stearyl alcohol, prepared by dissolving the stearyl alcohol in 50 mL of methanol, adding the polymer-salicylic acid combination to the stearyl alcohol solution, followed by evaporation of methanol on the rotary evaporator, and drying for one hour at 50° C.

Sample 3-a 1:0.41 ratio of POLYPORE™ E loaded with 67% salicylic acid to stearyl alcohol, prepared as Sample 1.

Sample 4-a 1:1.27 ratio of POLYPORE™ E loaded with 67% salicylic acid to stearyl alcohol, prepared as Sample 1.

A portion of each Sample 1–4 was placed into an aqueous phase. A control (uncoated) sample of POLYPORE™ E loaded with salicylic acid also was placed into an aqueous phase. Aliquots were taken at specified time intervals and analyzed by HPLC.

The results are summarized in FIG. 1, which shows that controlled release properties were substantially improved by adding a release retardant to the polymer-salicylic acid combination. It also was observed that a polymer-active agent combination coated with stearyl alcohol provided better controlled release properties than a combination coated with mineral oil. This improvement is attributed to the more hydrophobic nature of stearyl alcohol (i.e., an increased carbon chain length) and that stearyl alcohol is a solid at room temperature.

Obviously, many modifications and variations of the invention as hereinbefore set forth can be made without departing from the spirit and scope thereof and, therefore, only such limitations should be imposed as are indicated by the appended claims.

What is claimed is:

1. A composition comprising:
   (a) microparticles of an adsorbent polymer, said microparticles free of a monounsaturated monomer, and having a mean unit particle size of about 0.5 to about 80 microns and a bulk density of about 0.008 to about 0.1 gm/cc, and wherein the microparticles are prepared by a suspension polymerization process and are in the form of open spheres and sections of spheres;
   (b) an oil-soluble topically active compound, said active compound adsorbed onto said adsorbent polymer microparticles, wherein the active compound is present in a weight amount at least equal to and up to twenty times greater than the weight amount of the adsorbent polymer; and
   (c) a water-soluble release retardant, said release retardant coated and adsorbed onto said adsorbent polymer microparticles and said active compound.

2. The composition of claim 1 wherein the microparticles comprise at least two polyunsaturated monomers.

3. The composition of claim 2 wherein the polyunsaturated monomers comprise allyl methacrylate, ethylene glycol dimethacrylate, or a mixture thereof.

4. The composition of claim 3 wherein the adsorbent polymer comprises allyl methacrylate and ethylene glycol dimethacrylate in a weight ratio of about 1 to about 1.2.

5. The composition of claim 1 wherein the composition is a liquid, and the active compound is present in an amount of about 0.1% to about 30% by weight of the composition.

6. The composition of claim 1 wherein the composition is a solid, and the active compound is present in an amount of about 50% to about 95% by weight of the composition.

7. The composition of claim 1 wherein the composition is a semisolid, and the active compound is present in an amount of about 0.1% to about 75% by weight of the composition.

8. The composition of claim 1 wherein the topically active compound is selected from the group consisting of a skin-care compound, an antioxidant, and mixtures thereof.

9. The composition of claim 1 wherein the topically active compound is selected from the group consisting of aloe vera, PEG-4 dilaurate, lanolin oil, petrolatum, mineral wax, salicyclic acid, and mixtures thereof.

10. The composition of claim 1 wherein the topically active compound is selected from the group consisting of a silicone, isopropyl myristate, vitamin E acetate, retinol, and mixtures thereof.

11. The composition of claim 1 wherein the release retardant is present in an amount of about 0.5% to about 30% by weight of composition.

12. The composition of claim 1 wherein the release retardant is selected from the group consisting of a poly (acid) a polyol, a salt of a $C_8$–$C_{20}$ fatty acid, an alkanolamide, a water-soluble polymer, a biological polymer, a gum, a carbohydrate, a cellulose derivative, a sorbitan derivatives, and mixtures thereof.

* * * * *